(12) United States Patent
Rivas et al.

(10) Patent No.: US 7,376,238 B1
(45) Date of Patent: May 20, 2008

(54) PULSE RATE, PRESSURE AND HEART CONDITION MONITORING GLASSES

(75) Inventors: Victor A. Rivas, Lincoln, NE (US);
Richard Soltis, Cleveland, OH (US);
Lawrence E. Sternberg, Lincoln, NE (US)

(73) Assignee: Rivas Technologies International, Inc., Lincoln, NE (US)

( * ) Notice: Subject to any disclaimer, the term of this patent is extended or adjusted under 35 U.S.C. 154(b) by 0 days.

(21) Appl. No.: 09/396,888

(22) Filed: Sep. 16, 1999

Related U.S. Application Data

(60) Provisional application No. 60/101,138, filed on Sep. 18, 1998.

(51) Int. Cl.
*H04R 25/00* (2006.01)
*A61B 5/02* (2006.01)

(52) U.S. Cl. .................. 381/381; 600/500; 362/103

(58) Field of Classification Search .......... 381/67, 381/381, 327; 600/490–500, 528, 529, 530, 600/485, 344, 322–324; 362/103, 105, 276, 362/802

See application file for complete search history.

(56) References Cited

U.S. PATENT DOCUMENTS

| | | | |
|---|---|---|---|
| 4,164,937 A | | 8/1979 | Spencer |
| 4,260,951 A | | 4/1981 | Lewyn |
| 4,278,095 A | | 7/1981 | Lapeyre |
| 4,301,808 A | | 11/1981 | Taus |
| 4,658,831 A | * | 4/1987 | Reinhard et al. ........... 600/500 |
| 5,040,538 A | * | 8/1991 | Mortazavi .................. 600/333 |
| 5,064,410 A | * | 11/1991 | Frenkel et al. .............. 600/26 |
| 5,359,444 A | * | 10/1994 | Piosenka et al. ............ 349/13 |
| 5,431,170 A | * | 7/1995 | Mathews .................... 600/500 |
| 5,606,743 A | * | 2/1997 | Vogt et al. .................. 381/327 |
| 5,617,868 A | | 4/1997 | Harada et al. |
| 5,813,990 A | * | 9/1998 | Ryll ........................... 600/500 |
| 6,010,216 A | * | 1/2000 | Jesiek ........................ 381/327 |
| 6,123,661 A | * | 9/2000 | Fukushima et al. ......... 600/27 |
| 6,126,595 A | * | 10/2000 | Amano et al. ............. 600/500 |
| 6,431,705 B1 | * | 8/2002 | Linden ....................... 351/158 |

* cited by examiner

*Primary Examiner*—Xu Mei
(74) *Attorney, Agent, or Firm*—James Creighton Wray; Clifford D. Hyra

(57) ABSTRACT

Battery and solar cell powered health glasses monitor the condition of a heart's vital signs. Light emitting diodes (LED's) emit light into human temples. Photodiodes capture light reflected back from the pulsing blood. The amount of reflected light corresponds to the pulse rate. Embedded circuitry cleans and amplifies the signals, which are transmitted to light emitters located in the glasses. The same signals may be transmitted to a remote receiver to be processed and/or stored. Rhythm and shape of the pulse rate, processed on a home computer and available to doctors via the Internet, indicates heart condition. The circuits provide signal triangulation verification and warning lights. The sensors may be located any place on the body, i.e. wrist bands, chest, head, etc. A transmitter sends signals to the circuitry on the glasses to display reading information and lights about heart condition, pulse rate and blood pressure. Circuits on the glasses process and display electrical signals, pressure signals, pulse rate signals and combinations thereof.

26 Claims, 3 Drawing Sheets

PULSE RATE, PRESSURE AND HEART CONDITION MONITORING GLASSES

This application claims the benefit of U.S. Provisional Application No. 60/101,138, filed Sep. 18, 1998.

BACKGROUND OF THE INVENTION

Adverse heart conditions may lead to fatalities and long-term ill effects. Generally, the warning signs of an adverse heart condition are not realized in time to take preventive measures to lessen the long-term ill effects. The severity of the resulting problems due to an adverse heart condition may be lessened by an early determination of the onset of such a condition. A need exists for a heart condition monitor that detects adverse heart conditions early so that measures may be taken to lessen the long term ill effects resulting from the adverse heart condition.

SUMMARY OF THE INVENTION

Battery and solar cell powered health glasses monitor the condition of a heart's vital signs. Light emitting diodes (LED's) emit light into human temples. Photodiodes capture light reflected back from the pulsing blood. Blood vessels expand when the heart beats. The amount of reflected light corresponds to the pulse rate. Embedded circuitry cleans and amplifies the signals, which are transmitted to light emitters located in the glasses. The same signals may be transmitted to a remote receiver to be processed and/or stored. Rhythm and shape of the pulse rate, processed on a home computer and available to doctors via the Internet, indicates heart condition. The circuits provide signal triangulation verification and warning lights.

The sensors may be located any place on the body, i.e. wrist bands, chest, head, etc. A transmitter sends signals to the circuitry on the glasses to display reading information and lights about heart condition, pulse rate and blood pressure. Circuits on the glasses process and display electrical signals, pressure signals, pulse rate signals and combinations thereof.

These and further and other objects and features of the invention are apparent in the disclosure, which includes the a above and ongoing written specification, with the claims and the drawings.

DETAILED DESCRIPTION OF THE PREFERRED EMBODIMENTS

Figure 1:
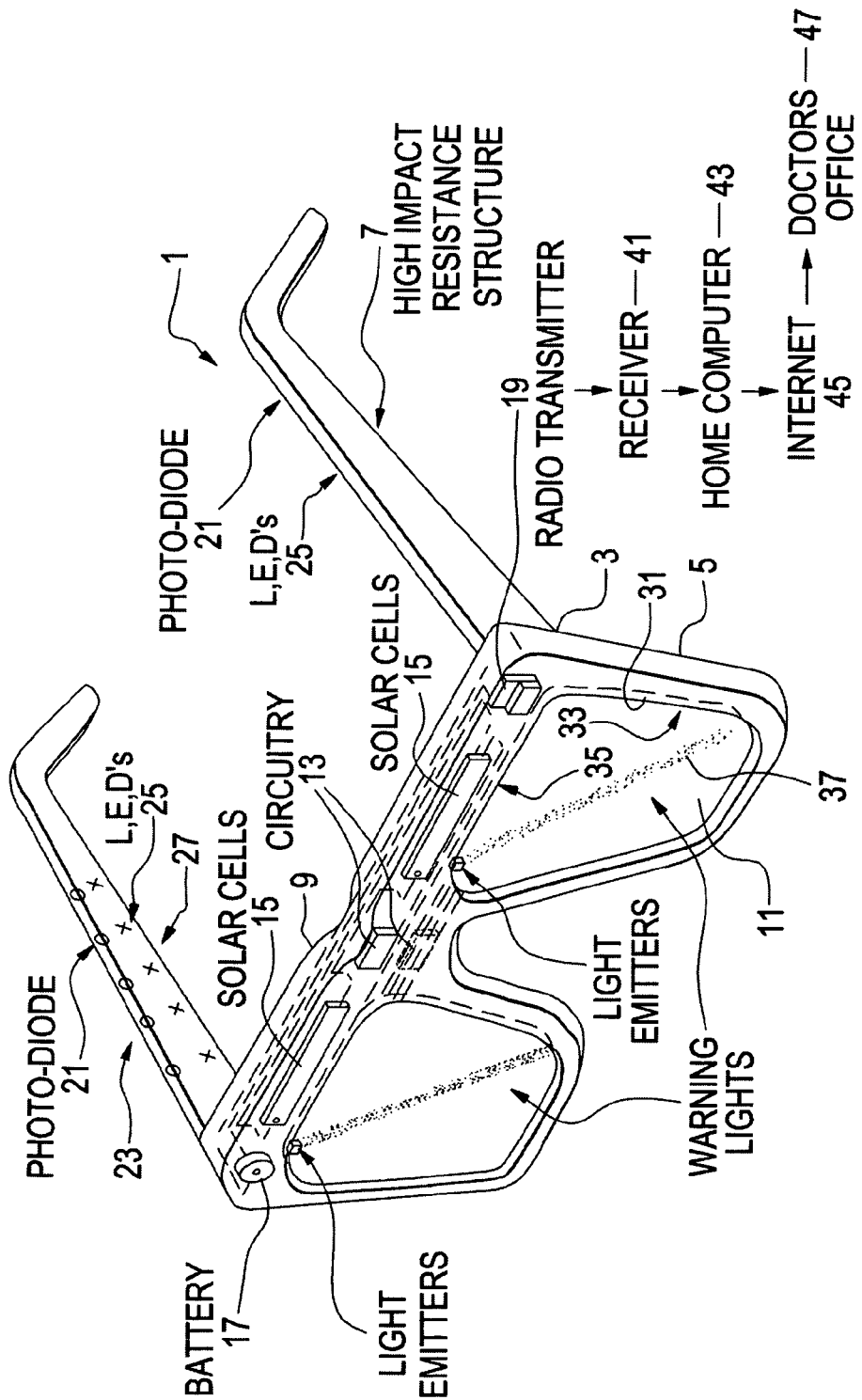
FIG. 1 is a schematic representation of glasses with sensors and displays.

Referring to FIG. 1, a pair of sensing and indicating glasses is generally indicated by the numeral 1. The glasses have frames 3 with frontal lens holder portions 5 and temple pieces 7. A bridge 9 above the lenses 11 contains electronic circuitry 13, solar cells 15, a battery 17, and a radio transmitter 19. Light emitting diodes (LED's) 21 are arranged in an array 23 along the insides of the temples. Photosensors 25 are arranged in an array 27 along the diodes and near the LED's 21, but not in direct light contact with the LED's 21. The LED's 21 produce light that is directed into the skin of the human temples near the area of the external carotid arteries. Light from the LED's is reflected to the photodiodes 25, either by being reflected by the skin or by being reflected after entering the arteries. The amount of light from the LED's returning to the photodiodes is periodically changed with each pulse. The change is sensed with the photodiodes that are connected to the circuitry 13, and the light from the pulse of the expanded artery is compared with the light from the relaxed arteries. The periodic rate is used by the circuitry 13 as a measure of pulse rate. The total light as compared to baseline, such as the lowest total light over a long period when the glasses are worn during a period of rest, provides a signal which is related to pulse rate or blood pressure.

Target quantities such as pulse rate may be input by conventional buttons that are mounted internally or externally on the frames 3. Alternatively, the radio transmitter 19 may be a transceiver, and target rates may be input by radio.

The glasses shown in FIG. 1 may have a complex or simplified form of heads-up displays that show numbers, such as by seven-segment displays or selective dot matrix illumination. Alternatively, the glasses have series of lamps 31 arranged in vertical arrays 33 and horizontal arrays 35 along the edges of the lens mounts. The lamps 31 may be illuminated individually and in groups to indicate pulse rate or blood pressure. The lamps may be of varied colors and may be focused to illuminate the glass in straight lines across the glass, or may be defocused to wash the glass with light. The light may be of uniform or select color. For example, a small green light in the corner may mean that the system is on, a yellow light diagonally across the corner may indicate that a target rate is being approached, and a white light 37 lower down and farther from the upper corner may indicate that a target rate has been reached. Lights causing a diagonal red line further down along the lens may indicate that a target has been exceeded, and purple illuminations diagonally across the centers of the lens may indicate that a target rate has been far exceeded, perhaps dangerously.

The radio transmitter 19 transmits to a receiver 41, which may be connected to a home computer 43, which in turn may be connected to the web 45 and thereby to a doctor's office 47. The computer 43 may connect to the web 45 upon exceeding of predetermined conditions, either above or below limits, so that an Internet connection may be used to alert a doctor's office 47. Alternatively, the Internet connection 45 may be used to alert an emergency service or an emergency number, such as 911. Under severe conditions, it is preferable to dial an emergency service or 911 before alerting a doctor's office.

Because exercise and muscle movements may be read as pulses, the invention uses signal triangulation verification.

Figure 2:
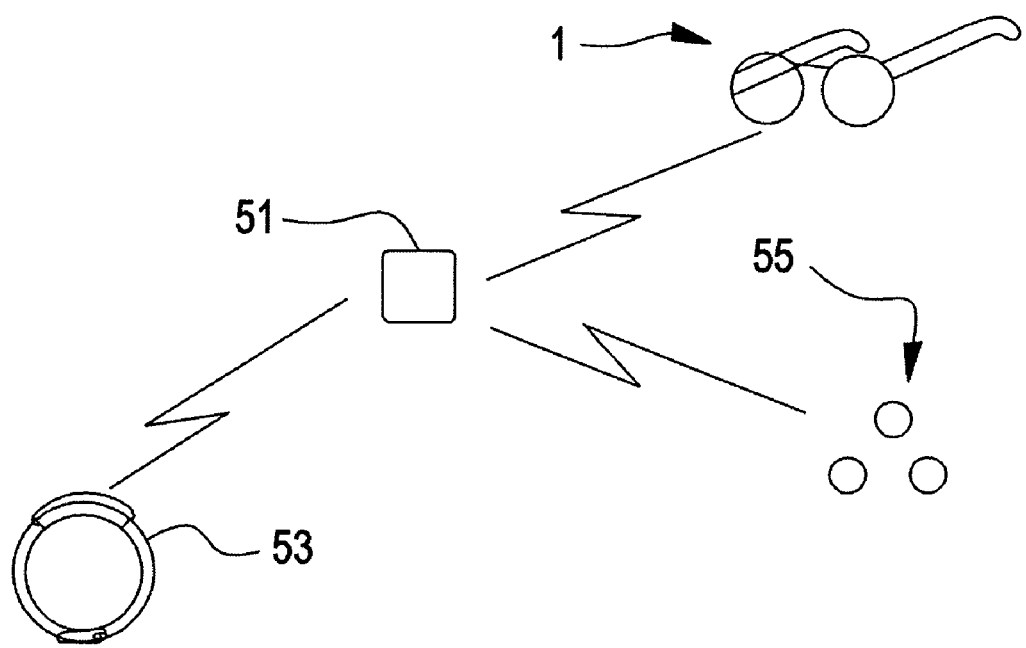
FIG. 2 is a schematic representation of the processing of signals.

FIG. 2 shows a signal discriminator chip 51 which is connected to the glasses 1 and to a watch 53 for receiving a pulse rate, and which is connected to electrodes 55 stuck on a chest or other positions on a body to determine heart rate. As an example, the electrodes 55 may sense breathing rate. The signal discriminator 51 is mounted on or connected to display glasses 1, either by radios or wires, to receive pulse rate and pressure signals from the glasses, the watch and the electrodes, and to provide signals for controlling displays.

Figure 3:
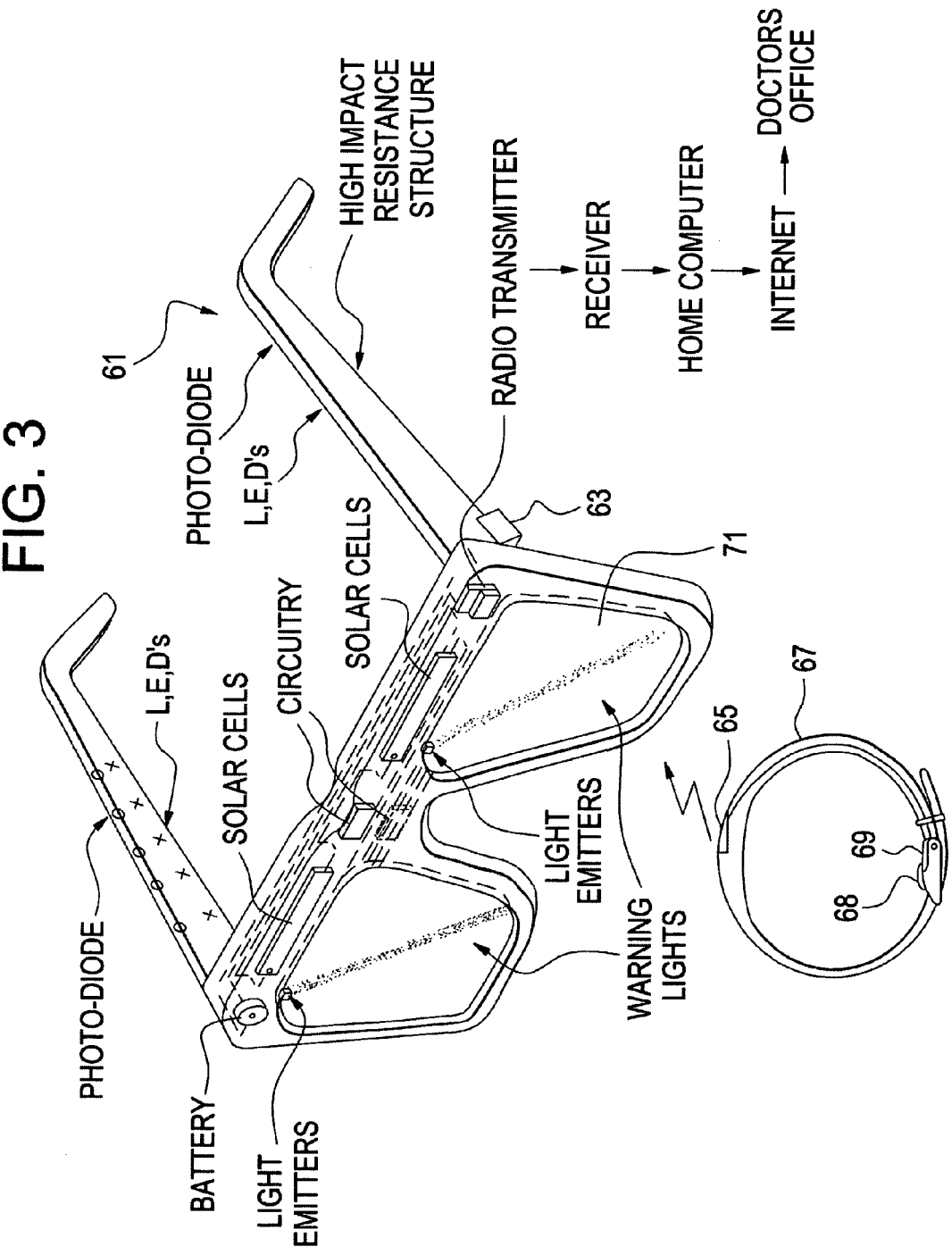
FIG. 3 is a schematic representation of glasses with displays and remote sensors.

As shown in FIG. 3, glasses 61 mount a radio receiver 63, which receives signals from a radio sender 65 mounted on a wrist watch band 67. A pulse sensor button 68 mounted on the inside of a watch strap buckle 69 is connected to the radio sender 65 to send pulse rate signals to the local radio receiver 63 mounted on the glasses 61. A matrix-type heads-up display of the type used in aviator or astronaut helmets displays numbers and directions. The lenses 71 may include several seven-segment or multiple element matrixes which are selectively energized and illuminated.

While the invention has been described with reference to specific embodiments, modifications and variations of the invention may be constructed without departing from the scope of the invention, which is defined in the following claims.

We claim:

1. Heart condition monitoring apparatus, comprising:
   a pair of glasses;
   a plurality of light emitting diodes on the glasses for emitting light onto a surface;
   a plurality of photosensors on the glasses for receiving reflected light;
   electronic circuitry on the glasses and connected to the plurality of photosensors for receiving signals from the plurality of photosensors;
   a power source on the glasses and connected to the plurality of light emitting diodes, the plurality of photosensors and the electronic circuitry for providing power; and
   wherein the plurality of photosensors are positioned in a plane offset from the plane of light emission from the light emitting diodes,
   further comprising a plurality of lamps on the pair of glasses for indicating a sensed condition of a user.

2. The apparatus of claim 1, wherein the power source is a battery.

3. The apparatus of claim 1, wherein the power source is at least one solar cell.

4. The apparatus of claim 1, further comprising:
   a battery as a back-up power source to the at least one solar cell.

5. The apparatus of claim 1,
   further comprising a transmitter on the glasses and connected to the circuitry for transmitting signals from the circuitry to a remote receiver.

6. The apparatus of claim 1, further comprising a display on lenses of the glasses for indicating the sensed condition of a user.

7. The apparatus of claim 1, wherein the display is a numerical display for indicating the user's heart rate and pulse rate.

8. The apparatus of claim 1, further comprising at least one button on the glasses for inputting the user's information.

9. Heart condition monitoring apparatus, comprising:
   a pair of glasses;
   a plurality of light emitting diodes on the glasses for emitting light onto a surface;
   a plurality of photosensors on the glasses for receiving reflected light;
   a plurality of electrodes positioned on a user's body for determining heart rate;
   a sensor on the user's wrist for determining pulse rate;
   a receiver on the glasses for receiving signals from the plurality of photosensors, from the plurality of electrodes and from the sensor; and
   a power source connected to the glasses for providing power to the plurality of light emitting diodes, the plurality of photosensors and the receiver.

10. The apparatus of claim 9, further comprising:
    a display on the lenses of the glasses for displaying signals transmitted by the receiver indicating a sensed condition of the user.

11. The apparatus of claim 10, wherein the display is a numerical display for indicating the user's pulse rate and heart rate.

12. The apparatus of claim 9, further comprising:
    a plurality of lamps on the glasses for indicating the sensed condition of the user.

13. The apparatus of claim 9, wherein the sensor is connected to a watch.

14. The apparatus of claim 13, further comprising a radio transmitter on the watch for transmitting signals from the sensor to the receiver.

15. The apparatus of claim 9, wherein the plurality of photosensors are positioned in a plane offset from the plane of light emission from the light emitting diodes.

16. The apparatus of claim 9, wherein the power source is a battery.

17. The apparatus of claim 9, wherein the power source is at least one solar cell.

18. The apparatus of claim 17, further comprising:
    a battery as a back-up power source to the at least one solar cell.

19. The apparatus of claim 9, wherein the receiver is a signal discriminator chip.

20. A method of monitoring heart condition, comprising:
    providing a pair of glasses;
    emitting light onto a surface of a user by a plurality of light emitting diodes on the glasses;
    receiving reflected light by a plurality of photosensors on the glasses;
    determining changes in the amount of reflected light received by the photosensors;
    transmitting a signal corresponding to the change in reflected light from the photosensors to circuitry on the glasses;
    determining a user's condition by measuring changes in the signals received by the circuitry, placing a sensor on the user's wrist;
    sensing the user's pulse rate by the sensor; and
    transmitting the pulse rate signal from the sensor to the circuitry on the glasses.

21. The method of claim 20, further comprising inputting target conditions to the circuitry;
    comparing the sensed condition to the target condition; and
    indicating to the user the relation between the sensed condition and the target condition.

22. The method of claim 21, wherein the indicating to the user comprises displaying a lighted display on the lenses of the glasses.

23. The method of claim 21, wherein the indicating to the user comprises displaying a numerical display on the lenses of the glasses.

24. The method of claim 20, further comprising:
    sending the signal from the circuitry to a transmitter;
    sending the signal from the transmitter to a remote receiver;
    sending the signal from the remote receiver to a home computer;
    determining if the sensed condition exceeds the user's inputted target condition; and
    sending the signal from the home computer to a doctor's office through the Internet when the sensed condition exceeds the target condition.

25. The method of claim 20, further comprising:
    sending the signal from the circuitry to a transmitter;
    sending the signal from the transmitter to a home computer;

determining if the sensed condition exceeds the user's inputted target condition by the home computer; and dialing an emergency service by the home computer when the sensed condition exceeds the target condition.

26. The method of claim 20, further comprising:

placing a plurality of electrodes on the user;

sensing the user's heart rate through the plurality of electrodes; and transmitting the heart rate signal from the plurality of electrodes to the circuitry on the glasses.

\* \* \* \* \*

UNITED STATES PATENT AND TRADEMARK OFFICE
CERTIFICATE OF CORRECTION

| | | |
|---|---|---|
| PATENT NO. | : 7,376,238 B1 | Page 1 of 1 |
| APPLICATION NO. | : 09/396888 | |
| DATED | : May 20, 2008 | |
| INVENTOR(S) | : Victor Rivas Alvarez et al. | |

It is certified that error appears in the above-identified patent and that said Letters Patent is hereby corrected as shown below:

Title Page, Item (12) "Rivas" should read --Rivas Alvarez, et al.--.

Title Page, Item (75) Inventors, "Victor A. Rivas" should read --Victor Rivas Alvarez--.

Signed and Sealed this

Twenty-ninth Day of November, 2011

David J. Kappos
*Director of the United States Patent and Trademark Office*